(12) United States Patent
Stefanchik et al.

(10) Patent No.: US 7,846,087 B2
(45) Date of Patent: Dec. 7, 2010

(54) ENDOSCOPIC ROTATION

(75) Inventors: David Stefanchik, Morrow, OH (US); James T. Spivey, Loveland, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 1025 days.

(21) Appl. No.: 11/380,952

(22) Filed: May 1, 2006

(65) Prior Publication Data
US 2007/0255096 A1 Nov. 1, 2007

(51) Int. Cl.
*A61B 1/00* (2006.01)
(52) U.S. Cl. .................................. 600/106; 600/104
(58) Field of Classification Search ............. 600/104, 600/106, 114, 115, 107, 127, 129, 137, 147–150, 600/153; 606/1, 129
See application file for complete search history.

(56) References Cited

U.S. PATENT DOCUMENTS

| | | | | |
|---|---|---|---|---|
| 5,007,406 A | * | 4/1991 | Takahashi et al. | ........... 600/119 |
| 5,390,940 A | * | 2/1995 | Morlino et al. | ............... 279/62 |
| 5,520,678 A | | 5/1996 | Heckele et al. | |
| 5,613,950 A | | 3/1997 | Yoon | |
| 6,358,267 B1 | * | 3/2002 | Murakami et al. | .......... 606/205 |
| 6,554,845 B1 | | 4/2003 | Fleenor et al. | |
| 6,997,931 B2 | | 2/2006 | Sauer et al. | |
| 7,052,492 B2 | | 5/2006 | Swanson et al. | |
| 7,150,752 B2 | * | 12/2006 | Suzuki et al. | ............... 606/141 |
| 2001/0025174 A1 | | 9/2001 | Daniel et al. | |
| 2003/0023141 A1 | | 1/2003 | Stelzer et al. | |
| 2004/0015054 A1 | * | 1/2004 | Hino | ........................... 600/146 |
| 2005/0033285 A1 | | 2/2005 | Swanson et al. | |
| 2005/0154261 A1 | * | 7/2005 | Ohline et al. | ............... 600/141 |
| 2005/0197623 A1 | | 9/2005 | Leeflang et al. | |
| 2005/0228224 A1 | * | 10/2005 | Okada et al. | ................ 600/104 |
| 2005/0234297 A1 | | 10/2005 | Devierre et al. | |
| 2006/0079889 A1 | | 4/2006 | Scott | |

FOREIGN PATENT DOCUMENTS

| | | |
|---|---|---|
| WO | WO2005081202 | 7/2004 |
| WO | WO2004054878 | 9/2005 |

OTHER PUBLICATIONS

Chinese Office Action for Application No. 200710107766.X, dated Feb. 12, 2010.

\* cited by examiner

*Primary Examiner*—John P Leubecker
*Assistant Examiner*—Victoria W Chen

(57) ABSTRACT

Devices and methods are provided for positioning a tool. In one embodiment, an endoscopic rotation device is provided having a rotatable collet, a flexible elongate translating mechanism, and an actuating mechanism. The rotatable collet can be configured to receive and engage a tool disposed therethrough, and the translating mechanism can be coupled to the collet. The actuating mechanism can be operatively associated with the translating mechanism and can be effective to cause the translating mechanism to apply a rotational force to the collet to rotate the tool disposed therethrough.

23 Claims, 13 Drawing Sheets

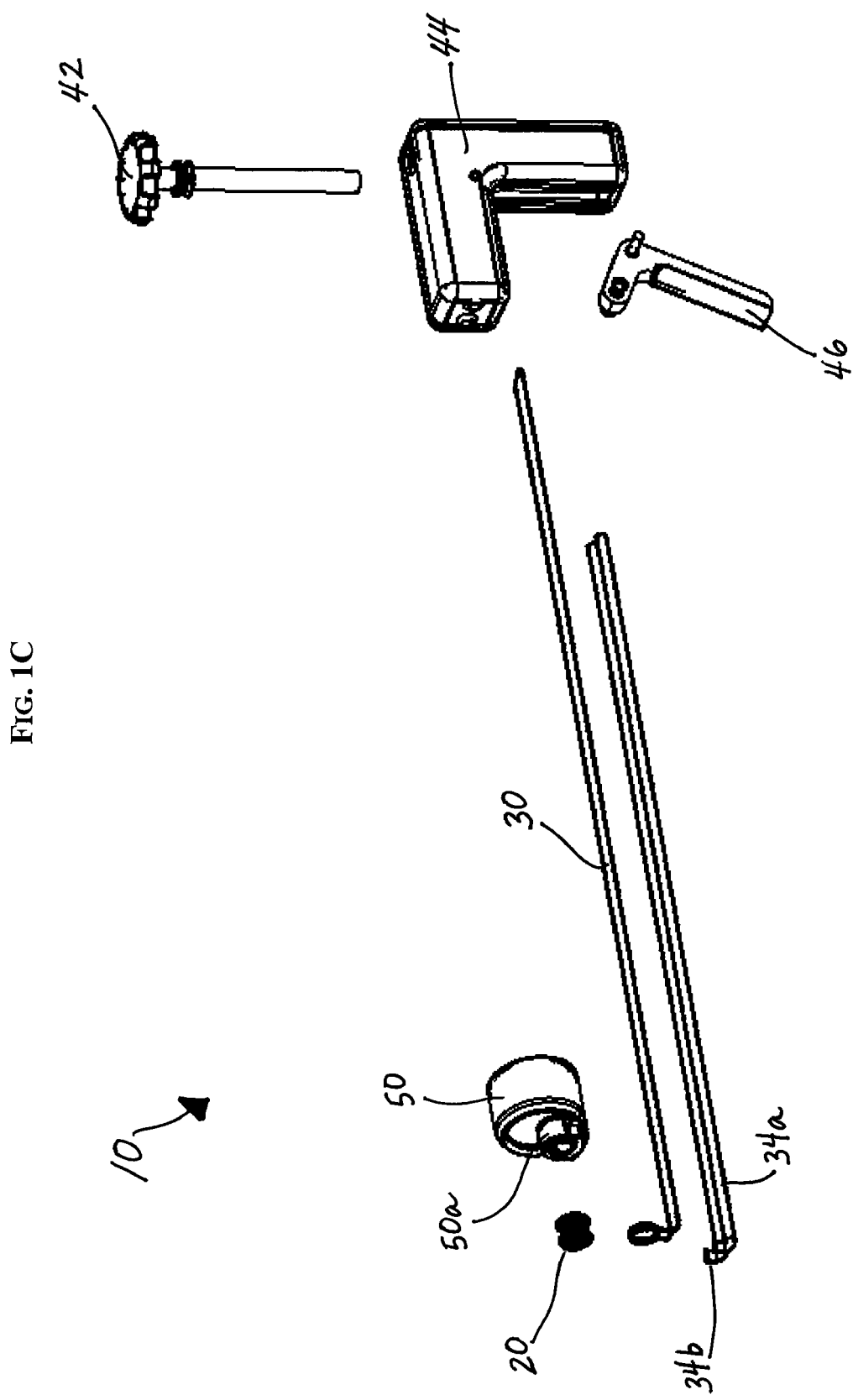

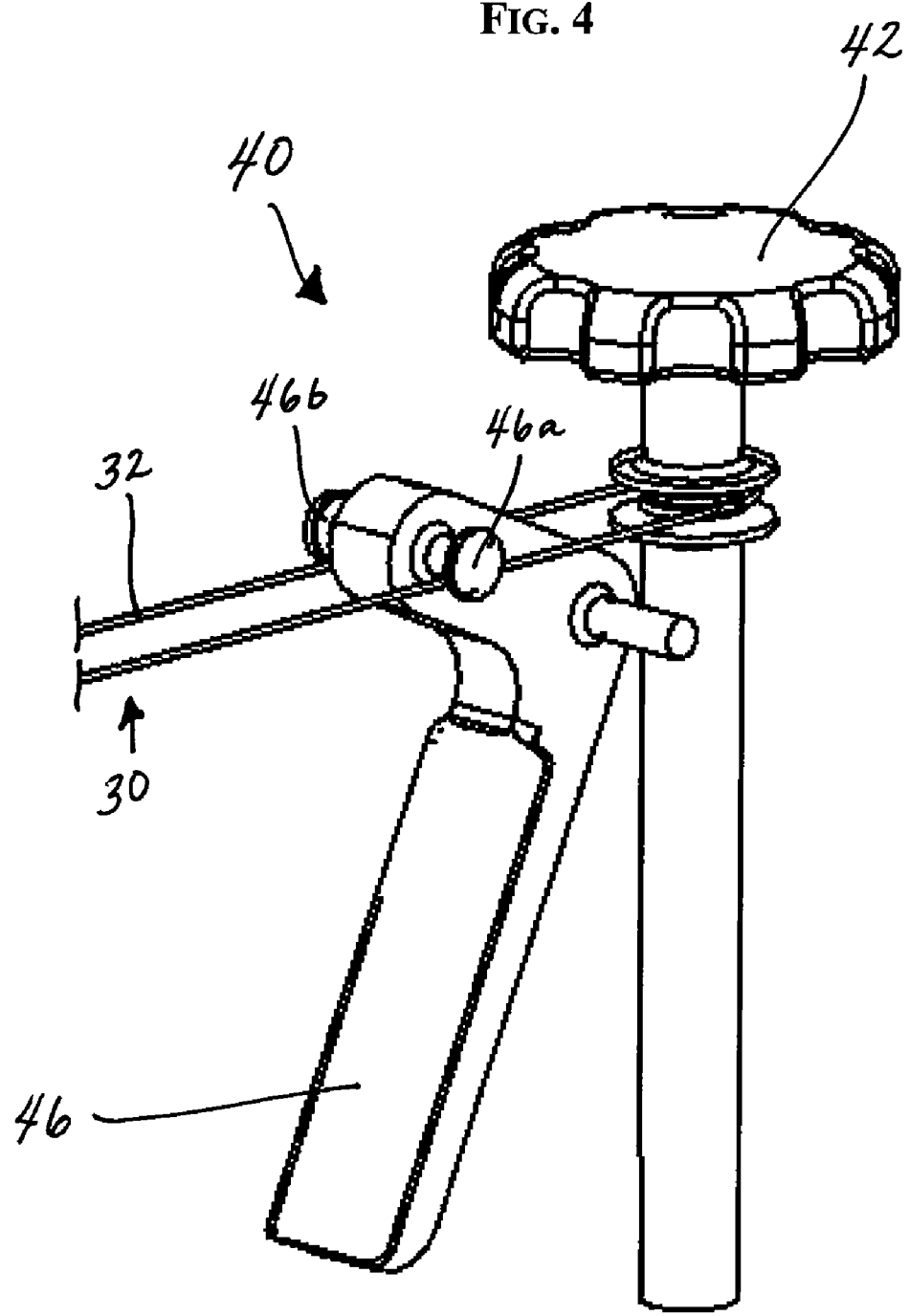

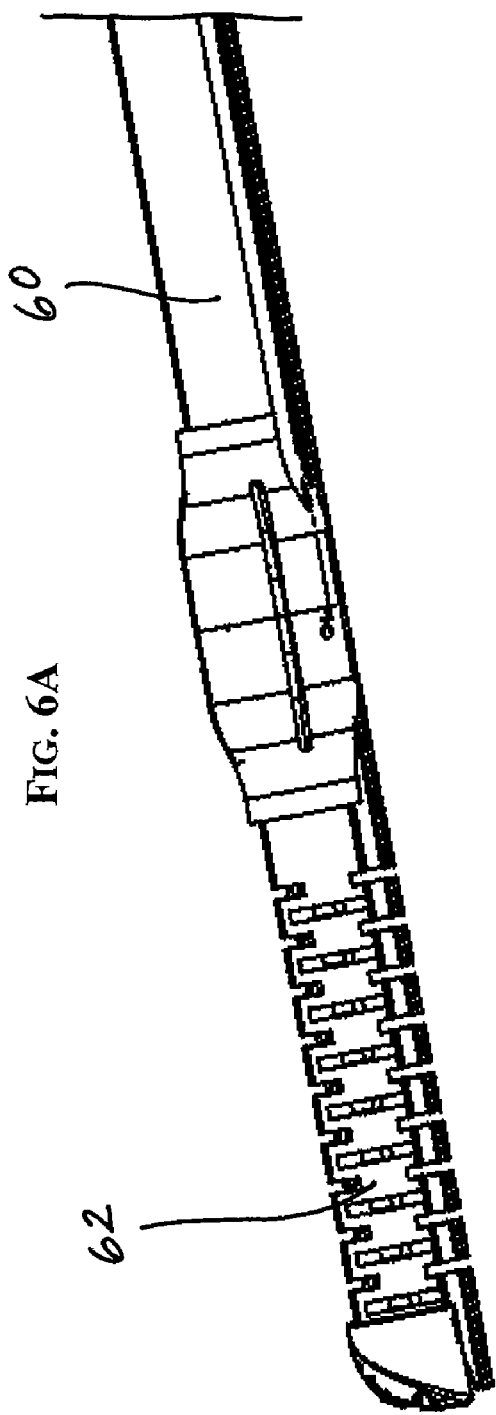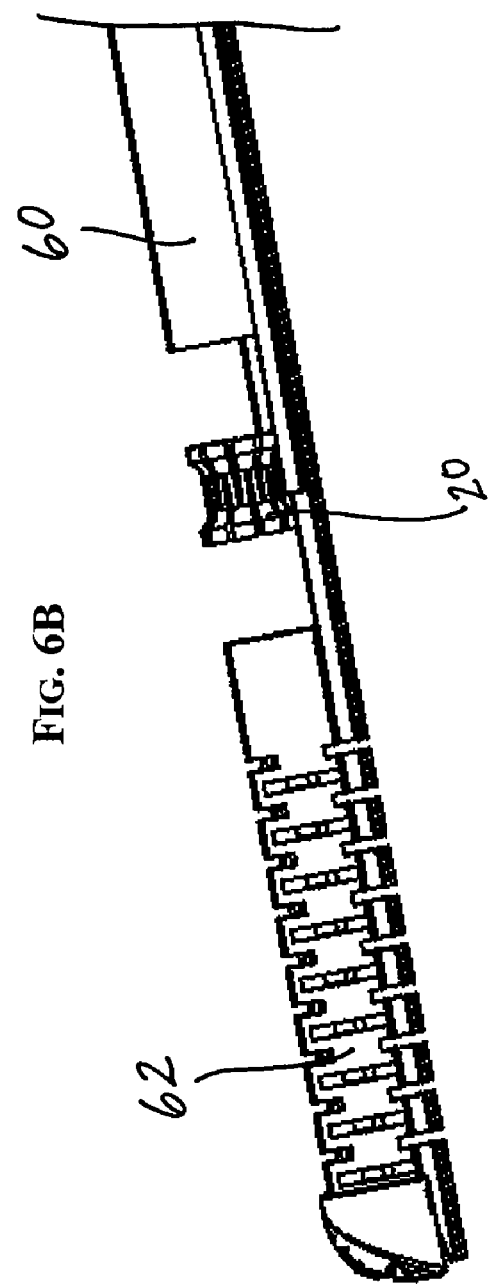

FIG. 8A
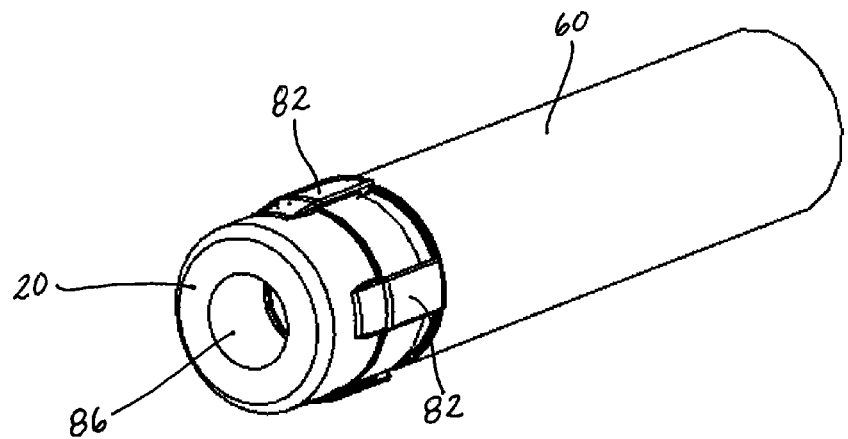
FIG. 8B
FIG. 8C
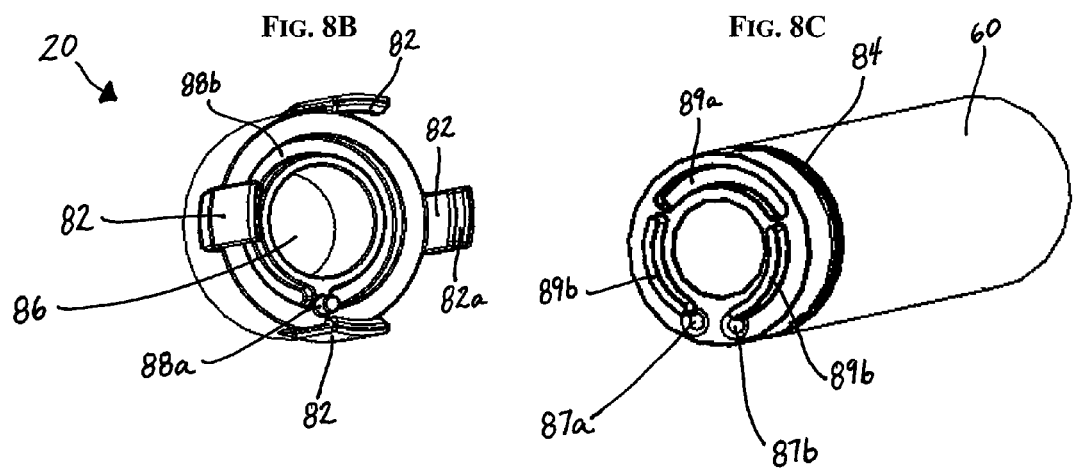

ENDOSCOPIC ROTATION

FIELD OF THE INVENTION

The present invention relates broadly to methods and devices for positioning a tool.

BACKGROUND OF THE INVENTION

Minimally invasive procedures are desirable because such procedures can reduce pain and provide relatively quick recovery times as compared with conventional open medical procedures. Many minimally invasive procedures are performed with an endoscope. Such procedures permit a physician to position, manipulate, and view medical instruments and accessories inside the patient through a small access opening in the patient's body. Laparoscopy is a term used to describe such an "endosurgical" approach using an endoscope (often a rigid laparoscope). In this type of procedure, accessory devices are often inserted into a patient through trocars placed through the body wall.

Still less invasive treatments include those that are performed through insertion of an endoscope through a natural body orifice to a treatment site. Examples of this approach include, but are not limited to, cystoscopy, hysteroscopy, esophagogastroduodenoscopy, and colonoscopy. Many of these procedures employ the use of a flexible endoscope during the procedure. Flexible endoscopes often have a flexible, steerable articulating section near the distal end that can be controlled by the user by utilizing controls at the proximal end.

Some flexible endoscopes are relatively small (1 mm to 3 mm in diameter), and may have no integral working channel. Other flexible endoscopes, including gastroscopes and colonoscopes, have integral working channels having a diameter of about 2.0 to 3.5 mm for the purpose of introducing and removing medical devices and other accessory devices to perform diagnosis or therapy within the patient. Certain specialized endoscopes are available, such as large working channel endoscopes having a working channel of 5 mm in diameter, which can be used to pass relatively large accessories. Other specialized endoscopes include those having two working channels. A separate accessory channel can also be used in conjunction with a conventional endoscope to facilitate the introduction of additional surgical tools or accessories.

One disadvantage of known systems is the lack of ability to precisely position the distal end of a tool disposed through a working channel of an endoscope or through an accessory channel mated to an endoscope.

Accordingly, a need exists for methods and devices for positioning a tool.

SUMMARY OF THE INVENTION

The present invention generally provides devices and methods for positioning a tool. In one embodiment, an endoscopic rotation device is provided having a rotatable collet, a flexible elongate translating mechanism, and an actuating mechanism. The rotatable collet can be configured to receive and engage a tool disposed therethrough, and the translating mechanism can be coupled to the collet. The actuating mechanism can be operatively associated with the translating mechanism and can be effective to cause the translating mechanism to apply a rotational force to the collet to rotate the tool disposed therethrough.

The collet can have a variety of configurations, and it can be rotatably disposed within a housing or directly mated to an endoscope, accessory channel, or sleeve adapted to mate to an endoscope and/or accessory channel. In one embodiment, the collet can have a fixed diameter and at least one grasping member disposed therein for engaging a tool extending therethrough. In another embodiment, the collet can have an adjustable diameter such that the diameter can be decreased to engage a tool extending therethrough.

The translating mechanism can also have a variety of configurations, but in one exemplary embodiment it can be at least one cable extending longitudinally between proximal and distal ends of the endoscopic rotation device. The translating mechanism can be slidably disposed through one or more elongate tubes. The elongate tubes can be coupled to an end cap or housing that has the collet rotatably disposed therein. Alternatively, the translating mechanism can be configured to extend within or external to an endoscope or accessory channel used with an endoscope. The distal end of the translating mechanism is preferably coupled to the collet, and in one embodiment the translating mechanism can be a cable loop that is wound around the collet. The proximal end of the translating mechanism can be operatively associated with an actuating mechanism at a proximal portion of the endoscopic rotation device for actuating the translating mechanism to rotate the collet.

The actuating mechanism can have a variety of configurations, but in one embodiment it can be disposed on a handle having the translating mechanism extending therethrough. The actuating mechanism can be in the form of, for example, a knob that is adapted to rotate to apply a translational force to the translating mechanism to rotate the collet. The handle can also include other features such as a trigger that is adapted to apply tension to the translating mechanism to decrease a diameter of the collet and allow the collet to engage a tool disposed therethrough.

In another aspect of the invention, a method for positioning a tool is provided and includes inserting an elongate member and a tool translumenally, positioning the tool through a rotatable collet associated with a distal portion of the elongate member, and actuating a translating mechanism to rotate the collet and thereby rotate the tool. In one embodiment, the elongate member can be an endoscope and the tool can be inserted therethrough. In another embodiment, the elongate member can be an accessory channel longitudinally coupled to an endoscope, and the tool can be inserted through the accessory channel. The translating mechanism can have various configurations, and in one embodiment it can be a cable actuator that is actuated by translating the cable axially along the elongate member such that translating the cable causes the collet to rotate. The cable can be translated by, for example, rotating a knob disposed on a handle. In another embodiment, a diameter of the collet can be decreased to engage a tool extending therethrough. For example, tension can be applied to the translating mechanism to cause a diameter of the collet to decrease. In particular, the translating mechanism can be a cable actuator wound around the collet and applying tension to the translating mechanism can include pivoting a trigger which pulls the cable actuator proximally.

In yet another aspect of the invention, a method of reconditioning the endoscopic rotation device is provided and includes replacing or cleaning at least a portion of at least one of the collet, translating mechanism, and actuating mechanism. The method can further include disassembling at least a portion of the device before the step of replacing or cleaning. The method can also include reassembling at least a portion of the device after the step of replacing or cleaning.

BRIEF DESCRIPTION OF THE DRAWINGS

The invention will be more fully understood from the following detailed description taken in conjunction with the accompanying drawings, in which:

FIG. 1C is an exploded view of the endoscopic rotation device shown in FIG. 1A;

FIG. 4 is a perspective view of a knob for rotating the collet of the endoscopic rotation device shown in FIG. 1A, and a trigger for decreasing a diameter of the collet of the endoscopic rotation device shown in FIG. 1A;

FIG. 6A is a perspective view of another embodiment of an endoscopic rotation device in the form of an accessory channel;

FIG. 6B is a perspective view of the accessory channel shown in FIG. 6A showing one embodiment of a collet disposed therein;

FIG. 8A is a perspective view of another embodiment of an endoscopic rotation device having a collet coupled to an accessory channel;

FIG. 8B is a perspective view of the collet shown in FIG. 8A;

FIG. 8C is a perspective view of the accessory channel shown in FIG. 8A with the collet removed;

DETAILED DESCRIPTION OF THE INVENTION

Certain exemplary embodiments will now be described to provide an overall understanding of the principles of the structure, function, manufacture, and use of the devices and methods disclosed herein. One or more examples of these embodiments are illustrated in the accompanying drawings. Those of ordinary skill in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

The present invention generally provides devices and methods for positioning a tool. The methods and devices utilize a rotatable collet that is configured to receive and engage a tool extending therethrough such that rotation of the collet is effective to rotate the tool, thereby providing the user with precise control over the position of the tool. The collet can be coupled to a distal end of a translating mechanism, and a proximal end of the translating mechanism can be associated with an actuating mechanism for actuating the translating mechanism. In particular, the actuating mechanism can cause the translating mechanism to slide axially and apply a rotational force to the collet to rotate the tool disposed therethrough. The collet, translating mechanism, and actuating mechanism can be incorporated into a variety of devices. For example, in one embodiment the collet can be formed on, attached to, or removably matable to a distal end of an endoscope for receiving one or more tools extending through the working channel of the endoscope. In another embodiment, the collet can be formed on, attached to, or removably matable to a distal end of an accessory channel adapted to mate to an endoscope, or sleeve adapted to mate to an endoscope and/or accessory channel. A person skilled in the art will appreciate that the collet can be used with a variety of surgical tools and devices, including various other endoscopic and laparoscopic tools and devices, as well as tools and devices used in other surgical procedures.

Figure 1A:
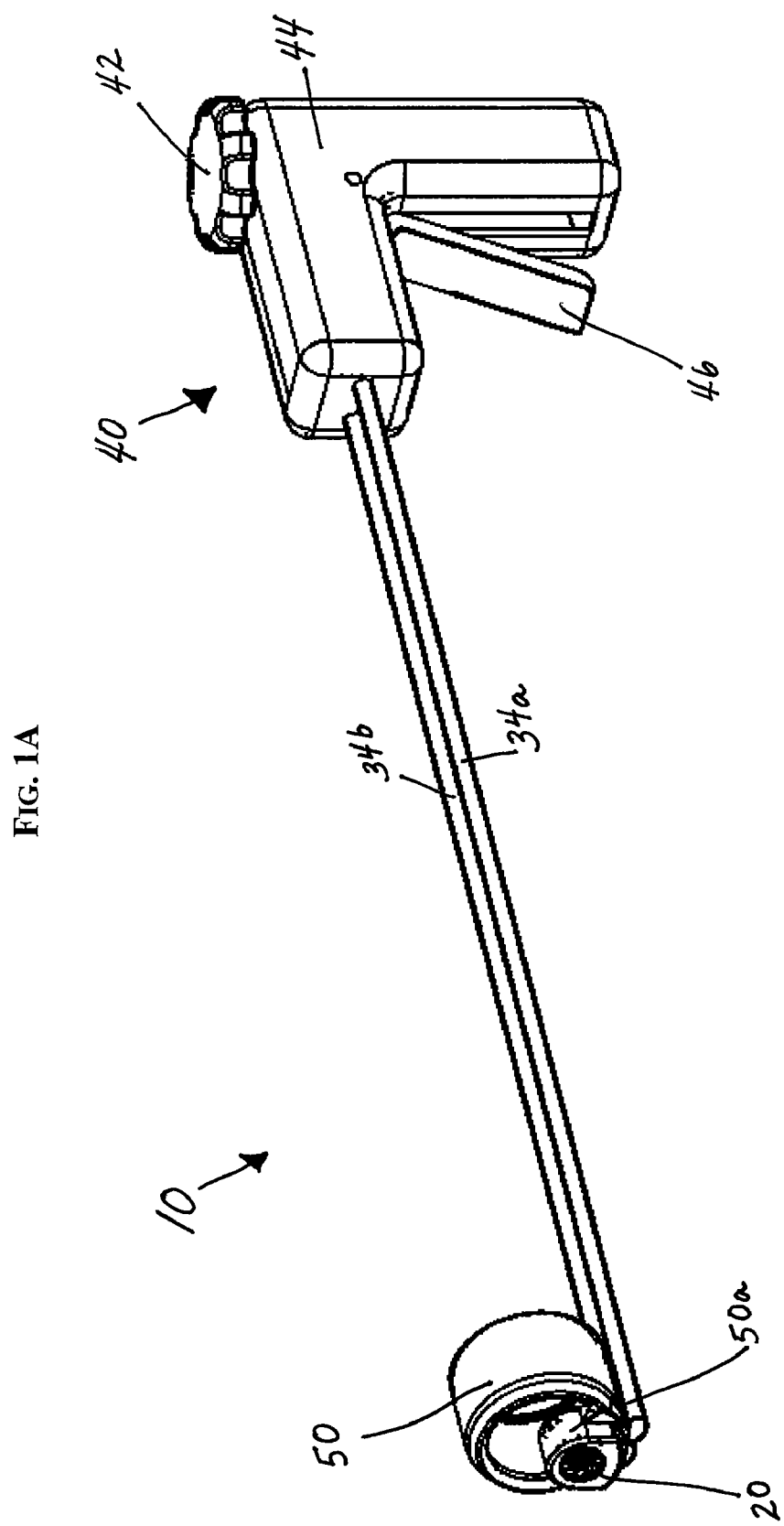
FIG. 1A is a perspective view of one embodiment of an endoscopic rotation device.
Figure 1B:
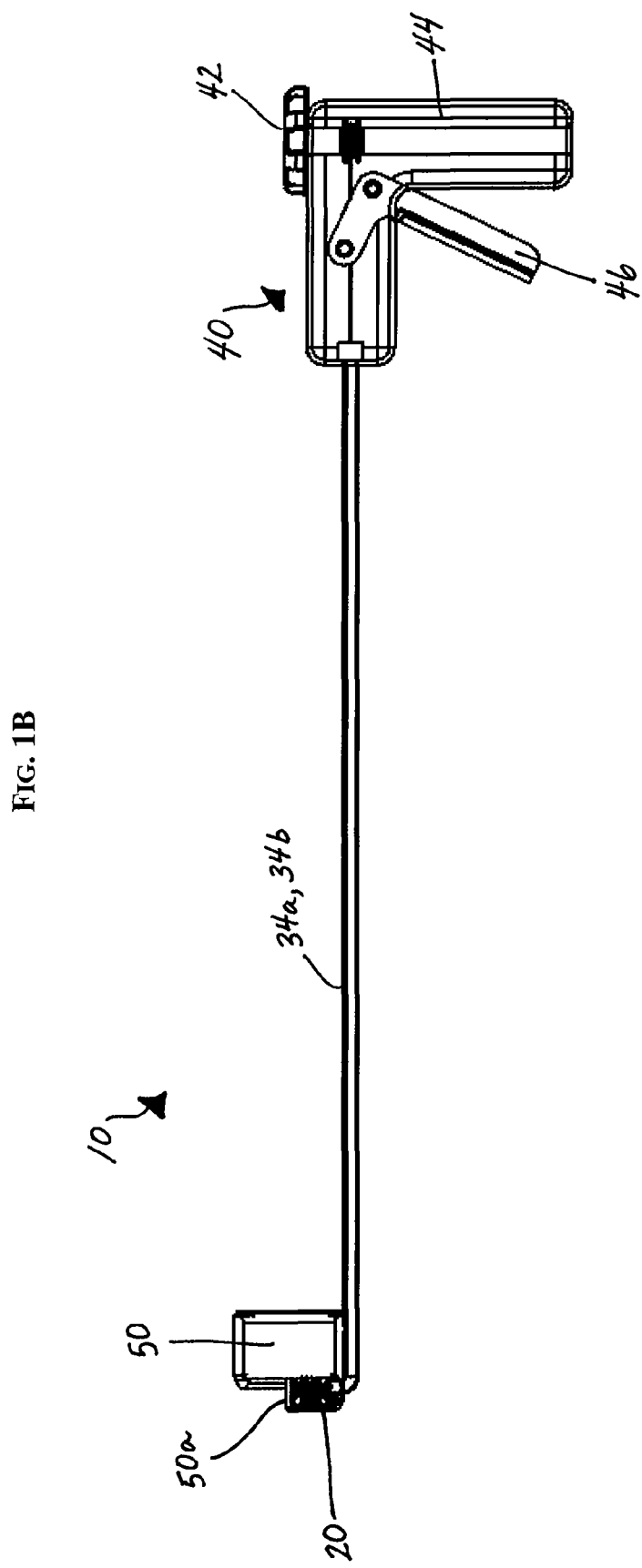
FIG. 1B is a cross-sectional view of the endoscopic rotation device shown in FIG. 1A.

FIGS. 1A-1C illustrate one exemplary embodiment of an endoscopic rotation device 10 for use with an endoscope and having a rotatable collet 20, a flexible elongate translating mechanism 30 (shown in FIG. 1C) coupled to the collet 20, and an actuating mechanism 40 for actuating the translating mechanism 30. In the illustrated embodiment, the collet 20 is rotatably disposed within a housing 50a which is disposed within an end cap 50 that is configured to removably mate to an endoscope. The translating mechanism 30 is slidably disposed within first and second elongate tubes 34a, 34b that are coupled to the end cap 50 at a distal end, and that are coupled to a handle 44 at a proximal end. A distal end of the translating mechanism 30 is coupled to the collet 20, and a proximal end extends into the handle 44 and is operatively associated with the actuating mechanism 40. The actuating mechanism 40 is effective to cause the translating mechanism 30 to apply a rotational force to the collet 20 to rotate a tool disposed therethrough. In use, the end cap 50 can slide over and mate to a distal portion of an endoscope, the elongate tubes 34a, 34b can be positioned axially along the endoscope, and the handle 44 can be positioned adjacent to the handle 44 of the endoscope. While not shown, one or more clamps can be provided to secure the elongate tubes 34a, 34b to the endoscope. The endoscopic rotation device can thus be used to rotate one or more tools or devices extending through a working channel of the endoscope.

Figure 2B:
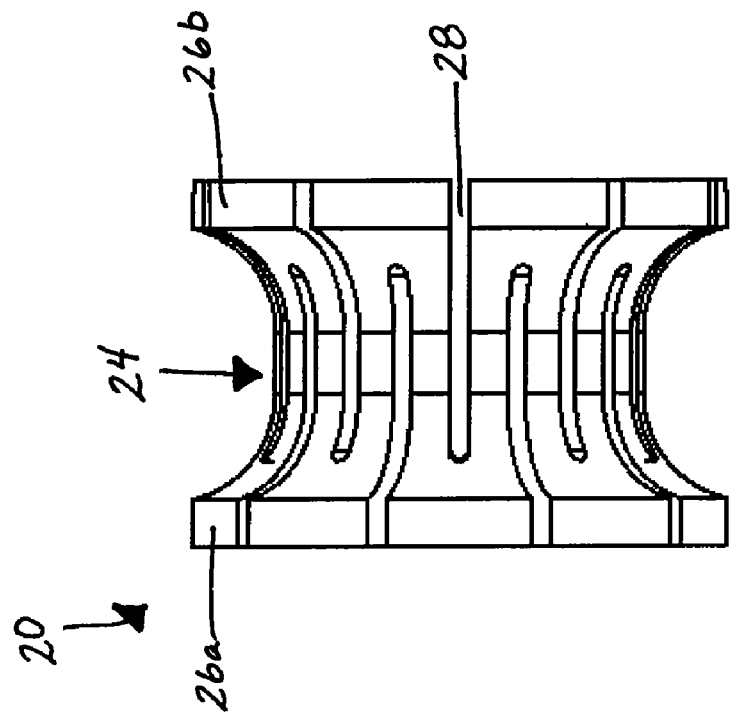
FIG. 2B is a side view of the collet shown in FIG. 2A.
Figure 2A:
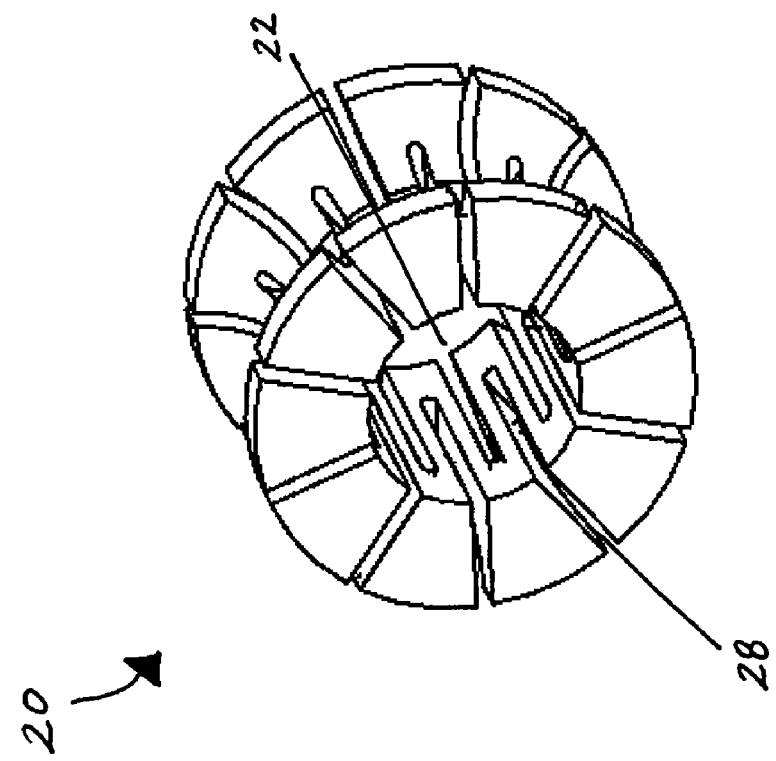
FIG. 2A is a perspective view of a collet of the endoscopic rotation device shown in FIG. 1A.

The collet 20 can have various shapes and sizes, but in one exemplary embodiment, as shown in more detail in FIGS. 2A and 2B, the collet 20 is in the form of a generally cylindrically shaped spool having an opening or bore 22 therethrough for receiving a tool. The collet 20 is shown with a cylindrical bore 22 extending therethrough, however the size and shape of the bore 22 can vary depending on the type of tool to be positioned and the desired use. The shape of the outer surface of the collet 20 can also vary, but it is preferably adapted to mate to the translating mechanism 30. In an exemplary embodiment, the translating mechanism 30 is in the form of an elongate flexible cable that is wound around the collet 20. Thus, the collet 20 can include a seating surface 24 for receiving the cable. While the shape of the seating surface 24 can vary, in an exemplary embodiment, the collet 20 has a concave seating surface 24 with opposed flanges 26a, 26b that extend outward from the collet 20. The concave shape of the seating surface 24 can pull the translating mechanism 30 toward the mid-portion of the surface as the collet 20 is rotated, thereby preventing the translating mechanism 30 from bunching or jumping over the opposed flanges 26a, 26b, becoming entangled, or otherwise inhibiting rotation of the collet 20.

As further shown in FIGS. 2A and 2B, the collet 20 can also have an adjustable diameter which can be decreased or increased to engage a tool extending therethrough. The diameter can be made adjustable using various techniques. In the illustrated embodiment, the collet 20 includes slits 28 cut into or formed therein to allow a diameter of the collet 20 to adjust. The slits 28 can extend from one flange to the other, terminating just short of the opposite flange. The slits 28 can also alternate so that one slit extends from one flange and the adjacent slit extends from the opposite flange. The number of slits can vary to obtain the desired expansion or contraction. The collet 20 can also be made from an elastically deformable material to further facilitate expansion and contraction of the collet. In use, the diameter of the collet 20 can optionally increase as it receives a tool (i.e., the collet 20 can stretch to receive a tool disposed therethrough) and/or the translating mechanism 30 can cause the diameter of the collet 20 to decrease (i.e., the translating mechanism 30 can tighten around the collet 20 causing the collet 20 to contract around a tool disposed therethrough) thereby enabling the collet 20 to engage a tool disposed therethrough. Various other exemplary collet configurations will be discussed in more detail below.

Figure 3A:
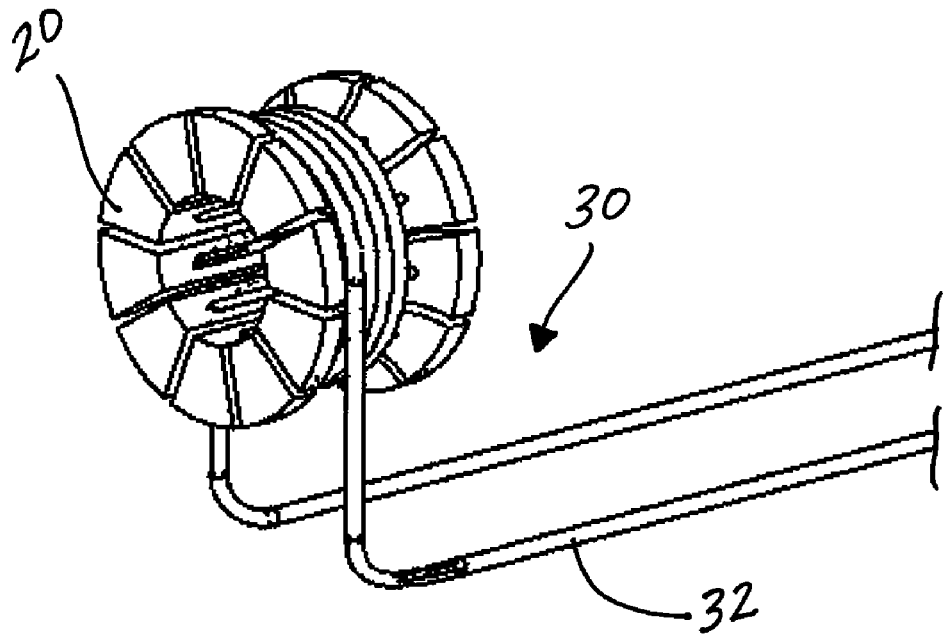
FIG. 3A is a perspective view of the collet shown in FIG. 2A coupled to a translating mechanism of the endoscopic rotation device shown in FIG. 1A.
Figure 3B:
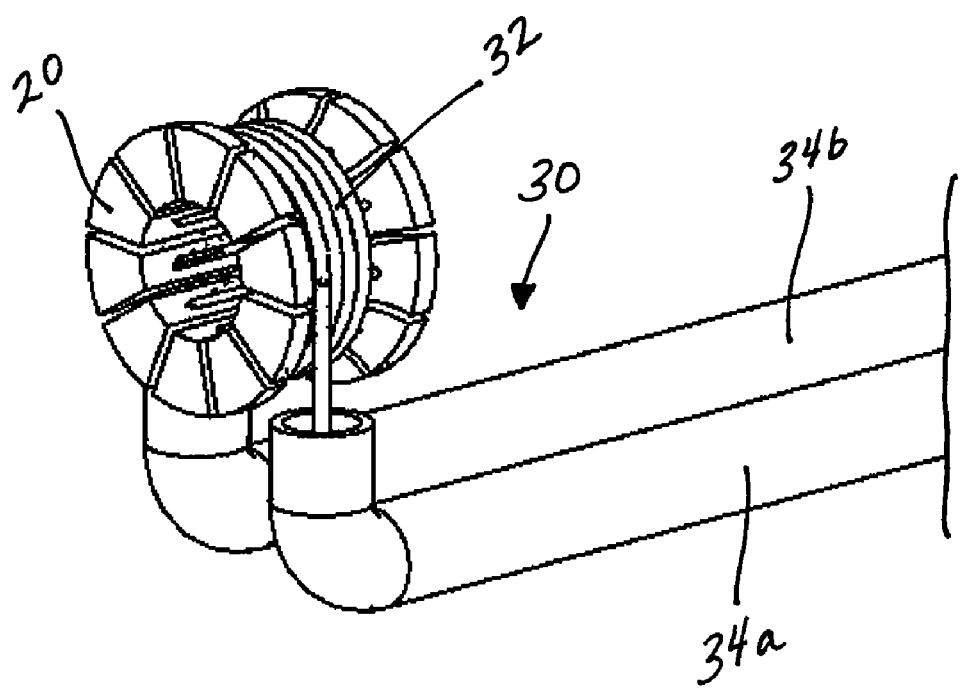
FIG. 3B is a perspective view of the collet and translating mechanism shown in FIG. 3A showing the translating mechanism disposed through first and second elongate tubes.

The translating mechanism 30 can also have a variety of configurations, but as indicated above, in an exemplary embodiment, the translating mechanism 30 is in the form of a single, continuous cable loop 32 having a distal portion that is wound around the collet 20. As shown in FIGS. 3A and 3B, the cable loop 32 can extend proximally from the collet 20, and can optionally be slidably disposed through first and second elongate tubes 34a, 34b (shown in FIG. 3B). A proximal portion of the cable can be operatively associated with an actuating mechanism 40 which will be discussed in more detail below. While the device is shown with a cable actuator 32, a person skilled in the art will appreciate that the translating mechanism 30 can also be in the form of a wire, braided rope, or other flexible cord. The translating mechanism 30 can be made from any flexible material suitable for being wound around a collet. In use, the translating mechanism 30 can slide along the longitudinal axis of the device, and the axial force can be converted to a rotational force to cause the collet 20 to rotate. As previously indicated, both ends or sides of the cable actuator 32 can also be tensioned to cause the cable 32 to tighten around the collet 20 and decrease a diameter of the collet 20 such that the collet 20 can engage a tool extending therethrough.

The actuating mechanism 40 of the device is preferably configured to apply a translational force to the translating mechanism 30 to slide the translating mechanism 30 along the longitudinal axis of the device 10. FIG. 4 illustrates one exemplary embodiment of an actuating mechanism 40 in the form of a knob 42 rotatably coupled to a handle or housing 44 of the device 10 for actuating the translating mechanism 30. In the illustrated embodiment, the translating mechanism 30, i.e., the cable actuator 32, is wound around the knob 42 such that rotation of the knob 42 will apply a rotational force to the translating mechanism 30 to cause it to translate axially through the tubes 34a, 34b. To increase the friction between the knob 42 and the mechanism 30 and to prevent the translating mechanism 30 from slipping, the knob 42 can include a sticky or textured surface and/or the translating mechanism 30 can be wound around the knob 42 multiple times.

The device 10 can also include a mechanism to apply tension to the translating mechanism 30 to decrease a diameter of the collet 20 and allow the collet 20 to engage a tool disposed therethrough. The tensioning mechanism can have a variety of configurations, but in one embodiment, shown in FIGS. 1A-1C and 4, the device 10 includes a trigger 46 pivotably coupled to the handle 44 and adapted to apply tension to the translating mechanism 30. As shown in FIG. 4, the trigger 46 can include protrusions 46a, 46b which extend from opposed sides of a top portion of the trigger 46, and which are positioned adjacent to the translating mechanism 30. In use, when the trigger 46 is pivoted, the protrusions 46a, 46b will apply a downward force on the translating mechanism 30 thereby tensioning the translating mechanism 30. As explained above, tensioning both sides of the translating mechanism 30 causes the translating mechanism 30 to tighten around the collet 20 thereby decreasing a diameter of the collet 20 and enabling the collet 20 to engage a tool disposed therethrough. A person skilled in the art will appreciate that a variety of other techniques can be used to apply tension to the translating mechanism 30. For example, the knob 42 can be configured to slide distally to tension the translating mechanism 30.

As indicated above, the endoscopic rotation device 10 can be used in conjunction with an endoscope, accessory channel, or other endoscopic or laparoscopic device. In the embodiment of FIGS. 1A-1C, the device 10 is configured to mate to an endoscope such that the collet is disposed at a distal end of the endoscope and is configured to receive and engage a tool extending through a working channel of the endoscope. Rotation of the collet is effective to rotate the tool, thereby providing the user with precise control over the position of the tool. In other embodiments, the device 10 can be used with an accessory channel mated to an endoscope. Accessory channels can be used in conjunction with endoscopes to facilitate the introduction and removal of surgical devices and accessories necessary for an endoscopic procedure. The collet 20 of the endoscopic rotation device 10 can be positioned at various locations along the length of an accessory channel. For example, in one exemplary embodiment shown in FIGS. 6A and 6B, the collet 20 is positioned proximal to a flexible articulating neck 62 formed on a distal end of an accessory channel 60. In another embodiment, shown in FIG. 7A, the collet 20 can be directly and removably mated to or formed on a distal end of the accessory channel 60. FIGS. 5A-8D illustrate several embodiments for coupling the device 10 to an endoscope 52 or accessory channel 60 and are discussed in detail below.

Figure 5A:
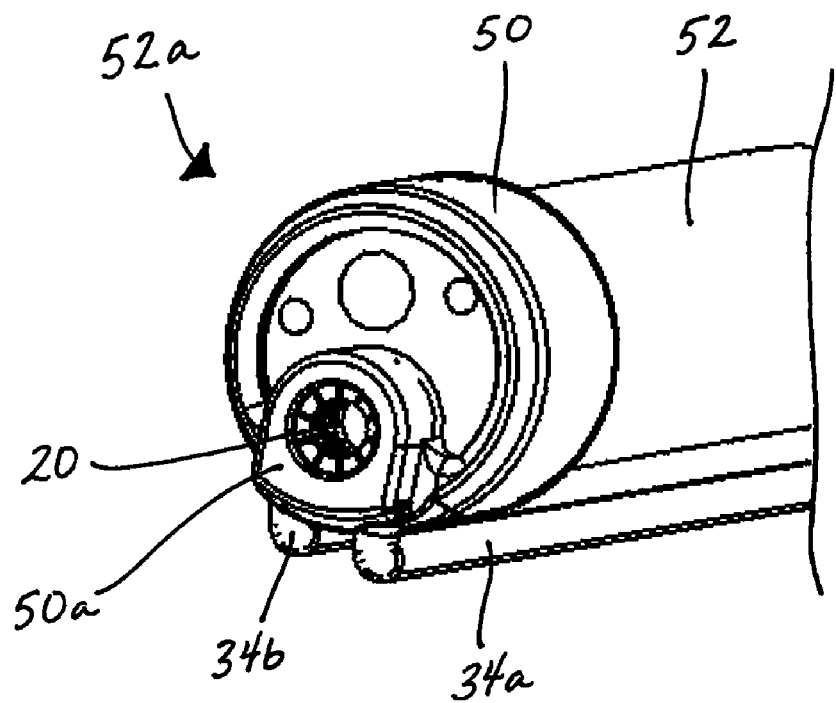
FIG. 5A is a perspective view of a distal portion of the endoscopic rotation device of FIG. 1A showing the device coupled to an endoscope.
Figure 5B:
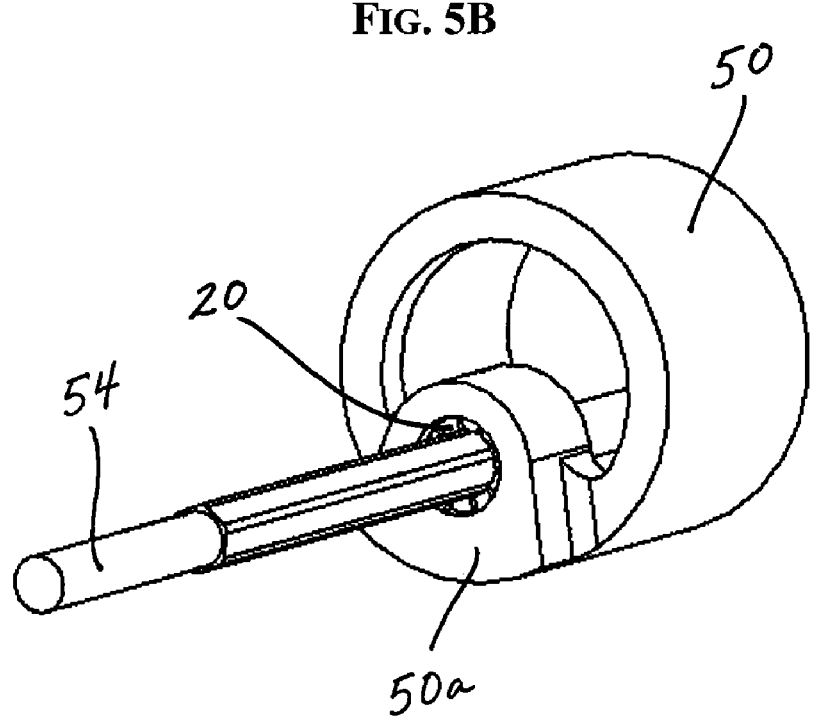
FIG. 5B is a perspective view of an end cap of the endoscopic rotation device of FIG. 1A showing a tool disposed therethrough.

A variety of configurations are available for mating the collet 20 to an endoscope, but in one exemplary embodiment shown in FIG. 5A, the collet 20 can be rotatably disposed within an end cap 50 adapted to mate to a distal end 52a of an endoscope 52. As shown, the end cap 50 is a generally cylindrical shaped sleeve or collar that is adapted to slide over or otherwise removably mate to a distal end 52a of an endoscope 52. Although the end cap 50 embodiment is shown and described in conjunction with an endoscope, a person skilled in the art will appreciate that the end cap 50 can also be removably matable to or formed on an accessory channel or a sleeve slidably disposable over an endoscope. The end cap 50 can include a smaller cylindrical housing 50a formed therein or coupled thereto for housing the collet 20. The smaller housing 50a can be offset from the center of the cap 50 such that it is aligned with a working channel of the endoscope 52, and it can also be sized such that it does not interfere with the viewing element of the endoscope 52. Alignment can be achieved by rotating the end cap 50 until the bore 22 of the collet 20 is aligned with the working channel. The smaller housing 50a can also include openings configured to allow the translating mechanism 30 to pass into the housing 50a to engage the collet 20. As shown in FIG. 5A, the openings can be in communication with the elongate tubes 34a, 34b which house the translating mechanism 30. In the illustrated embodiment, the elongate tubes 34a, 34b run along the outside the endoscope 52. In another embodiment, the elongate tubes 34a, 34b can be disposed within a working channel of the endoscope 52. In yet another embodiment, the translating mechanism 30 itself can extend through a working channel or run along side an outer surface of the endoscope 52. As shown in FIG. 5B, in use, a tool 54 can be inserted through the smaller housing 50a of the end cap 50 and be engaged by the collet 20 to facilitate rotation of the tool 54.

There are also a variety of configurations for mating the collet 20 to an accessory channel. For example, as shown in FIGS. 6A and 6B, the collet 20 can be rotatably coupled to or disposed within a portion of an accessory channel 60. The accessory channel 60 can be adapted to mate externally to an endoscope 52 or to a sleeve disposed over an endoscope using. For example, a track and rail can be formed on the accessory channel 60 and the endoscope 52 or sleeve, and the rail can slide in the track to extend along the length of the accessory channel 60 or endoscope 52. The accessory channel 60 can also have a lumen extending therethrough for receiving at least one tool, and optionally a flexible articulating neck 62 for positioning a tool disposed therethrough. As shown, the collet 20 can be coupled to a portion of the channel 60 that is proximal to the flexible articulating neck 62. The translating mechanism 30 can extend proximally from the collet 20 through or along the accessory channel 60, and, as described above, can be operatively associated with an actuating mechanism for applying a translational force to the translating mechanism 30.

Figure 7A:
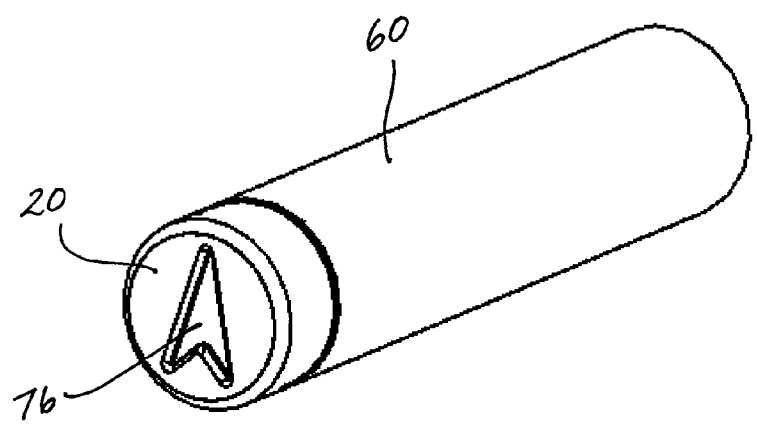
FIG. 7A is a perspective view of another embodiment of an endoscopic rotation device having an accessory channel with a collet rotatably coupled to a distal end thereof.
Figure 7B:
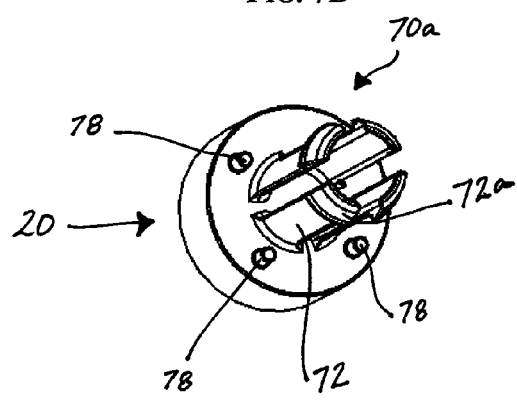
FIG. 7B is a perspective view of the collet shown in FIG. 7A.

In another embodiment, the collet 20 can be removably mated to or formed on a distal-most end of an accessory channel. FIGS. 7A-8D illustrate exemplary embodiments for directly and removably coupling the collet 20 to an accessory channel 60. In these embodiments, the collet 20 is not housed in an end cap 50 but instead is in the form of a rotatable end cap that directly mates to the accessory channel 60. Although this embodiment is shown and described as a collet 20 that mates directly to an accessory channel 60, a person skilled in the art will appreciate that the collet 20 can also be configured to mate to an endoscope 52 or a sleeve adapted to be disposed over an endoscope 52. As shown in FIG. 7B, the collet 20 can include a mating element 70a formed thereon and adapted to removably mate to a complementary mating element 70b formed on the accessory channel 60. In the illustrated embodiment, the collet 20 has deflectable prongs 72 formed thereon for mating to a lumen 74 of the accessory channel 60. The deflectable prongs 72 can include lips 72a that are adapted to snap the collet 20 into the lumen 74 and secure the collet 20 to the accessory channel 60 while allowing the collet 20 to rotate. Other mating techniques that allow free rotation of the collet relative to the accessory channel can be used. As further shown, the collet 20 has a keyed arrowhead shaped slot 76. Such a shape can facilitate engagement of a tool extending therethrough without the need to decrease the diameter of the opening. The keyed slot 76 can have various shapes and sizes and can be formed from an elastic material to allow the slot 76 to stretch to engage a tool disposed therethrough.

Figure 7C:
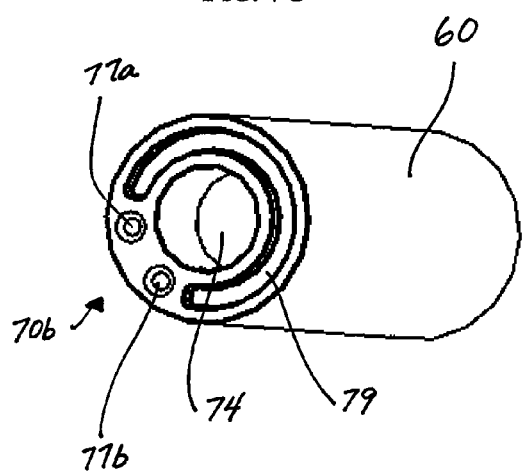
FIG. 7C is a perspective view of the accessory channel shown in FIG. 7A with the collet removed.
Figure 7D:
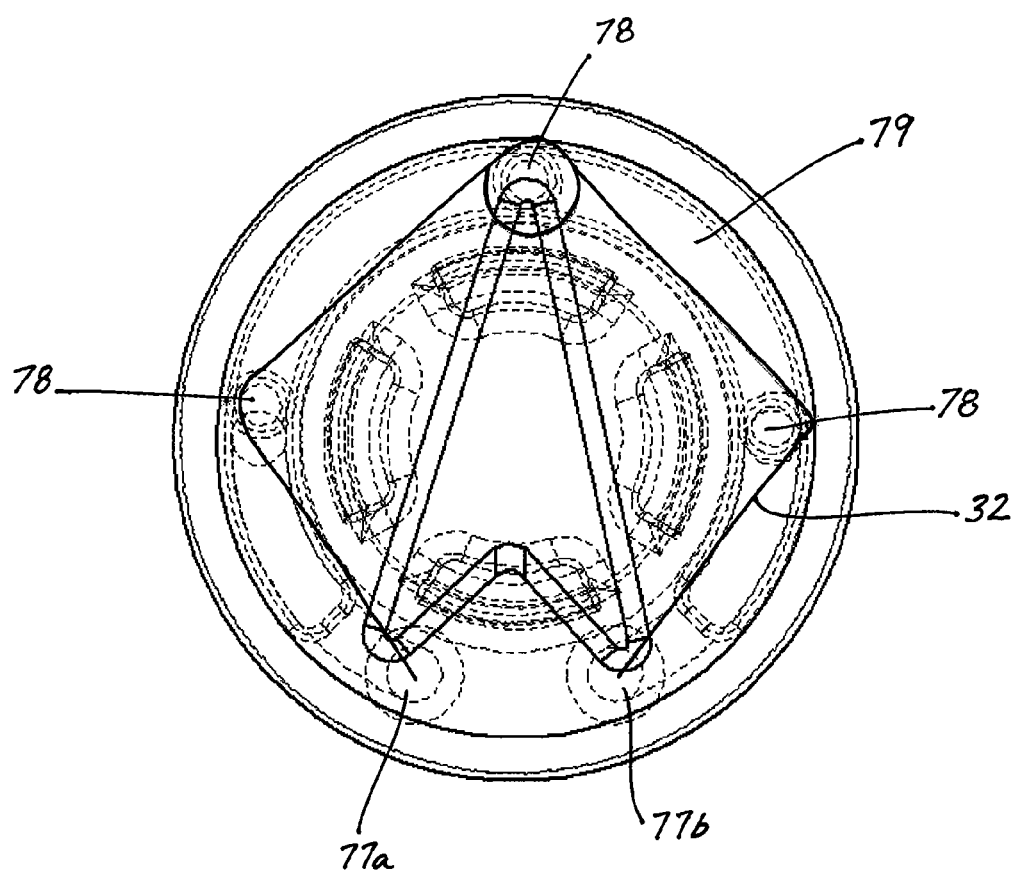
FIG. 7D is a cross-sectional end view of the collet and accessory channel shown in FIG. 7A.

The embodiment illustrated in FIGS. 7A-7D can also include features to facilitate rotational movement of the collet 20. As shown in FIG. 7C, the distal end of the accessory channel 60 can include at least one outlet (two outlets 77a, 77b are shown) for the translating mechanism 30. The collet 20 can also include one or more pins 78 formed thereon and adapted to be slidably received within a c-shaped groove 79 formed in the distal end of the accessory channel 60. As illustrated in FIG. 7D, the translating mechanism 30 can extend from the first outlet 77a, around the pins 78 which can be received by the groove 79 in the accessory channel 60, and into the second outlet 77b. The translating mechanism 30 can be translated axially along the accessory channel 60 to rotate the collet 20 in a path defined by the groove 79. To enable the translating mechanism 30 to engage and rotate the collet 20, the pins 78 can be shaped to receive the translating mechanism 30, they can have a sticky or textured surface, or other techniques can be used to generate friction or mate the translating mechanism 30 and pins.

Another configuration for rotatably mating a collet 20 to an accessory channel 60 is illustrated in FIGS. 8A-8D. Although this embodiment is shown and described as a collet 20 mated directly to an accessory channel 60, a person skilled in the art will appreciate that the collet 20 can also be mated directly to an endoscope 52 or a sleeve adapted to be disposed over an endoscope 52. In this embodiment, the collet 20 includes deflectable prongs 82 formed on an outer surface thereof for mating to an accessory channel 60. The deflectable prongs 82 have lips 82a that are adapted to snap into a groove 84 formed around an outer surface of the distal portion of the accessory channel 60 such that the collet 20 is secured the accessory channel 60 but allowed to rotate. As shown, the collet 20 has a keyed cylindrical slot 86. Similar to the embodiment described above, such a shape can facilitate engagement of a tool extending therethrough without the need to decrease the diameter of the opening. The slot 86 can have various shapes and sizes, and can also be formed from an elastic material to allow the slot 86 to stretch to engage a tool disposed therethrough.

Figure 8D:
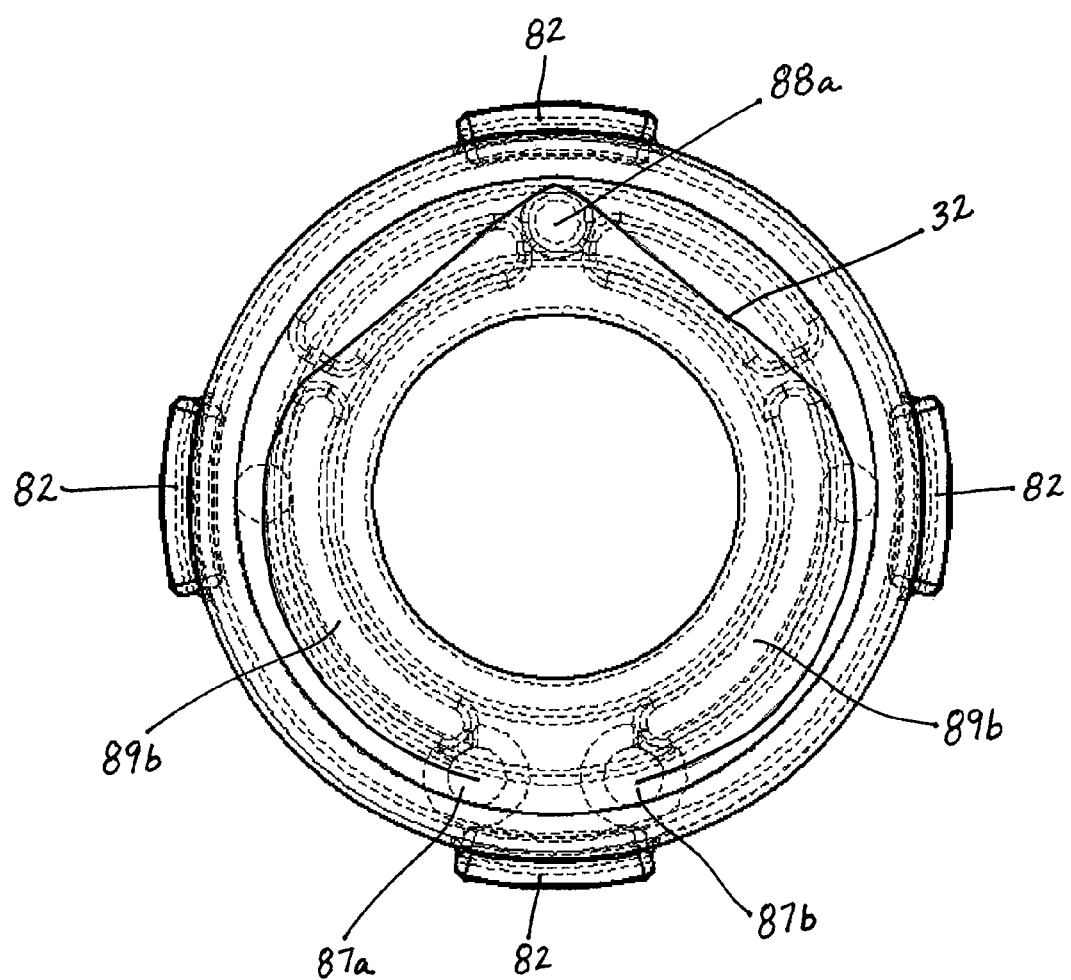
FIG. 8D is a cross-sectional end view of the collet and accessory channel shown in FIG. 7A.

The embodiment shown in FIGS. 8A-8C can also include features for facilitating the rotational movement of the collet 20. For example, as shown in FIG. 8B, the collet 20 can include both a pin 88a formed thereon and a circular groove formed therein 88b. The distal end of the accessory channel 60, shown in FIG. 8C, can include both a groove 89a and two arc-shaped protrusions 89b. The pin 88a of the collet 20 is adapted to be slidably received by the groove 89a formed in the accessory channel 60, and the protrusions 89b of the accessory channel 60 are adapted to be received by the groove 88b formed in the collet 20. A person skilled in the art will appreciate that a number of pin and groove configurations can guide the rotation of the collet 20. As illustrated in FIG. 8D, the translating mechanism 30 can extend from a first outlet 87a, pass over the protrusions 89b formed on the accessory channel 60, wind around the pin 88a formed on the collet 20, and extend into a second outlet 87b. The translating mechanism 30 can be translated axially to rotate the collet 20 in a path defined by the grooves 88b, 89a formed in the collet 20 and the accessory channel 60, respectively. As previously explained, to enable the translating mechanism 30 to engage and rotate the collet 20, the pin 88a and/or protrusions 89b can be shaped to receive the translating mechanism 30, they can have a sticky or textured surface, or other techniques can be used to generate friction or mate the translating mechanism 30 and pins.

Figure 9:
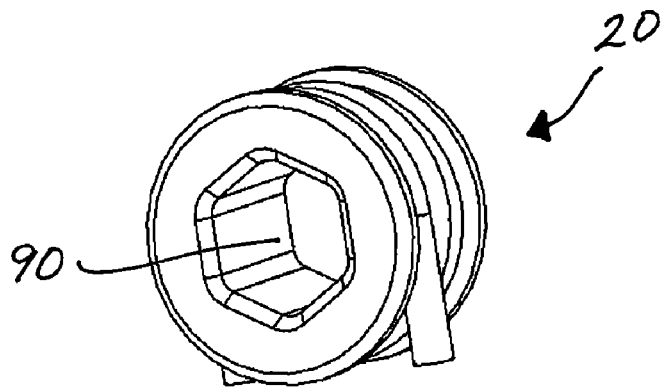
FIG. 9 is a perspective view of yet another embodiment of a collet for use with an endoscopic rotation device.
Figure 10:
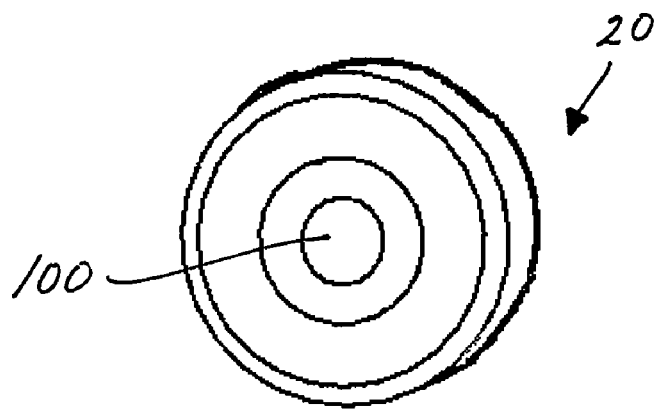
FIG. 10 is a perspective view of another embodiment of a collet for use with an endoscopic rotation device.
Figure 11:
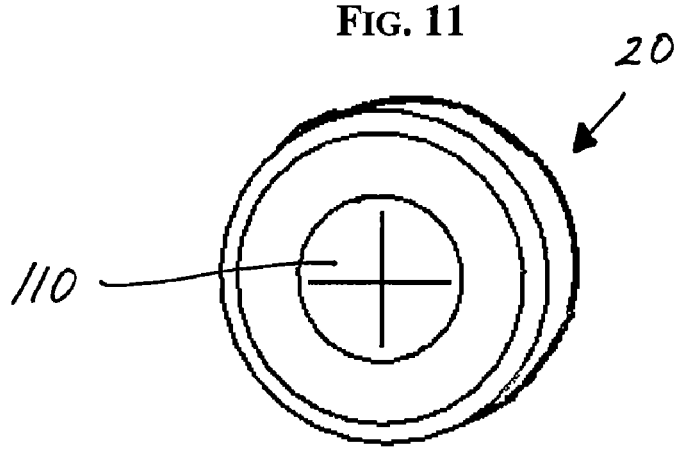
FIG. 11 is a perspective view of yet another embodiment of a collet for use with an endoscopic rotation device.

A person skilled in the art will appreciate that any of the collets disclosed herein can be incorporated into any and all embodiments of the endoscopic rotation devices disclosed herein. FIGS. 9-11 illustrate additional exemplary collet 20 embodiments. The collet 20 shown in FIG. 9 has a keyed hexagonal bore 90 extending therethrough for receiving a tool. FIG. 10 illustrates a collet 20 having a seal 100 disposed therein and adapted to expand to engage a tool disposed therethrough. A collet 20 having a flexible duck bill valve 110 is shown in FIG. 11. The duck bill valve 110 is adapted to engage a tool inserted therethrough. Other embodiments, not shown, can include a collet 20 having a star-shaped configuration with prongs for grasping a tool extending therethrough, a split o-ring configuration adapted to decrease in diameter when engaged by the translating mechanism 30, and any other configuration that allows a tool to be inserted through and engaged by the collet.

The present invention also provides methods for positioning a tool. In one exemplary embodiment, a tool 54 (shown in FIG. 5B) can be inserted translumenally through an elongate member (not shown) to position a distal end of the tool 54 through a rotatable collet 20 of an endoscopic rotation device 10. Once the device 10 is positioned in the body proximate to the procedure site (e.g., positioned in the stomach for any number of gastric procedures), a knob 42 disposed on a handle 44 of the actuating mechanism 40 can be rotated to translate the translating mechanism 30 axially along the elongate member, thereby rotating both the collet 20 and the tool 54 disposed therethrough. Where provided, a trigger 46 disposed on the handle 44 of the actuating mechanism 40 can also optionally be actuated to apply tension to the translating mechanism 30 and cause the collet 20 to contract and engage the tool 54 disposed therethrough.

In another exemplary embodiment, the endoscopic rotation device 10, or portions thereof, can be designed to be disposed of after a single use, or it can be designed to be used multiple times. In either case, however, the device can be reconditioned for reuse after at least one use. Reconditioning can include any combination of the steps of disassembly of the device, followed by cleaning or replacement of particular pieces, and subsequent reassembly. By way of example, the endoscopic rotation device and its components shown in FIGS. 1A-11 can be reconditioned after the device has been used in a medical procedure. The device can be disassembled, and any number of the particular pieces (e.g., the collet 20, the translating mechanism 30, or the actuating mechanism 40) can be selectively replaced or removed in any combination. For instance, the collet 20 can be replaced by a new collet 20, while the remaining pieces are sterilized for reuse. Replacement of pieces can also include replacement of portions of particular elements. Upon cleaning and/or replacement of particular parts, the device can be reassembled for subsequent use either at a reconditioning facility, or by a surgical team immediately prior to a surgical procedure. Those skilled in the art will appreciate that reconditioning of an endoscopic rotation device can utilize a variety of techniques for disassembly, cleaning/replacement, and reassembly. Use of such techniques, and the resulting reconditioned endoscopic rotation device 10, are all within the scope of the present application.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. An endoscopic rotation device, comprising:
   a rotatable collet having an adjustable diameter and an inner lumen defining a central axis extending longitudinally therethrough, the collet being configured to decrease in diameter to receive and engage a tool disposed therethrough;
   a flexible elongate translating mechanism including a cable loop wound around the collet; and
   an actuating mechanism operatively associated with the translating mechanism and effective to cause the translating mechanism to rotate the collet circumferentially about the central axis and to apply a rotational force to the collet to rotate the tool disposed therethrough.

2. The device of claim 1, wherein the translating mechanism is slidably disposed through at least one elongate tube.

3. The device of claim 2, wherein the translating mechanism comprises at least one cable extending between proximal and distal ends of the elongate tube and coupled to the collet.

4. The device of claim 1, wherein the flexible elongate translating mechanism comprises first and second tubes and wherein the cable loop is slidably disposed through the first and second tubes.

5. The device of claim 4, wherein the first and second tubes are coupled to an end cap having the collet rotatably disposed therein.

6. The device of claim 1, wherein the collet is rotatably disposed within a housing.

7. The device of claim 6, wherein the housing is adapted to mate to a distal end of an endoscope.

8. The device of claim 7, further comprising a sleeve coupled to the housing and adapted to be slidably disposed over the endoscope.

9. The device of claim 6, wherein the housing is formed adjacent a distal end of an accessory channel adapted to mate externally to an endoscope and having a lumen extending therethrough for receiving at least one tool.

10. The device of claim 9, wherein the accessory channel is mated to a sleeve adapted to be disposed over an endoscope.

11. The device of claim 1, wherein the actuating mechanism is disposed on a handle coupled to a proximal end of an elongate tube having the translating mechanism extending therethrough.

12. The device of claim 11, wherein the actuating mechanism comprises a knob adapted to rotate to apply a translation force to the translating mechanism to rotate the collet.

13. The device of claim 11, wherein the handle includes a trigger adapted to apply tension to the translating mechanism to decrease a diameter of the collet.

14. An endoscopic rotation device, comprising:
   a rotatable collet having an adjustable diameter and an inner lumen defining a central axis extending longitudinally therethrough for receiving a tool, the collet being adapted to couple to a distal portion of an endoscope for insertion through a body lumen;
   an elongate translating mechanism adapted to extend longitudinally along an endoscope and having a first end adapted to remain outside of a patient's body and a second end including a cable loop extending around the collet;

a first actuator coupled to the first end of the elongate translating mechanism and effective to translate the translating mechanism relative to an endoscope, wherein translation of the translating mechanism rotates the collet circumferentially about the central axis and is effective to rotate the collet.

15. The device of claim 14, wherein the collet is adapted to couple to an endoscope to rotate a tool extending longitudinally relative to the endoscope.

16. The device of claim 14, wherein the cable loop extends from the first actuator and around the collet.

17. The device of claim 14, further comprising a second actuator positioned to apply tension to the translating mechanism, wherein tension applied to the translating mechanism is effective to decrease a diameter of the collet to engage a tool extending therethrough.

18. A method for positioning a tool, comprising:
inserting an elongate member translumenally;
inserting a tool translumenally to position a distal end of the tool through a rotatable collet associated with a distal portion of the elongate member, the collet engaging the tool;
applying tension to a translating mechanism to decrease a diameter of the collet to engage the tool extending therethrough; and
actuating the translating mechanism coupled to the collet to rotate the collet circumferentially about a longitudinal axis of the tool and thereby rotate the tool within a body lumen.

19. The method of claim 18, wherein the elongate member comprises an endoscope and the tool is inserted through the endoscope, the collet being rotatably associated with a distal end of the endoscope.

20. The method of claim 18, wherein the elongate member comprises an endoscope and the tool is inserted through an accessory channel longitudinally coupled to the endoscope, the collet being rotatably associated with a distal portion of the accessory channel.

21. The method of claim 18, wherein the translating mechanism comprises a cable actuator and actuating the translating mechanism comprises translating the cable actuator axially along the elongate member, the cable actuator being coupled to the collet such that translation of the cable actuator rotates the collet.

22. The method of claim 21, further comprising rotating a knob disposed on a handle to translate the cable actuator axially along the elongate member.

23. The method of claim 18, wherein the translating mechanism comprises a cable actuator wound around the collet and applying tension to the translating mechanism comprises pivoting a trigger which pulls the cable actuator proximally.

* * * * *